(12) United States Patent
Stamatas (10) Patent No.: US 8,150,501 B2
(45) Date of Patent: Apr. 3, 2012

(54) METHOD FOR MEASURING SKIN ERYTHEMA

(75) Inventor: Georgios Stamatas, Issy-les Moulineaux (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 551 days.

(21) Appl. No.: 12/411,642

(22) Filed: Mar. 26, 2009

(65) Prior Publication Data

US 2010/0249731 A1 Sep. 30, 2010

(51) Int. Cl.
*A61B 6/00* (2006.01)
(52) U.S. Cl. .......................... 600/477; 600/476
(58) Field of Classification Search ............... 600/476, 600/477, 475
See application file for complete search history.

(56) References Cited

U.S. PATENT DOCUMENTS

| | | | |
|---|---|---|---|
| 6,907,193 B2* | 6/2005 | Kollias et al. ............... 396/4 |
| 6,961,517 B2* | 11/2005 | Merola et al. ............... 396/14 |
| 6,984,228 B2* | 1/2006 | Anderson et al. ............ 606/9 |
| 7,477,767 B2* | 1/2009 | Chhibber et al. ............ 382/128 |
| 2005/0030372 A1* | 2/2005 | Jung et al. ............... 348/77 |
| 2005/0049467 A1* | 3/2005 | Stamatas et al. ........... 600/315 |
| 2007/0237374 A1* | 10/2007 | Nikiforos et al. ............ 382/128 |

OTHER PUBLICATIONS

Dolotov, L, E., et al. Digital Imaging of Human Skin, Proceedings of the Spie—the International Society for Optical Engineering Spie—In. Soc., Opt. Eng. US vol. 5067, No. 1., 2003, pp. 139-147.
Byungjo-Jung, "Polarization Spectral Imaging System for Quantitative Evaluation of Port Wine Stain Blanching Following Laser Treatment", journal of the Optical society of Korea, Opt. Soc. Korea south Korea, vol. 7, No. 4, Dec. 2003, pp. 234-239.
Leachwenauer, J., et al. "A Non-Contact Imaging-Based Approach to Detecting Stage 1 Pressure Ulcers", Engineering in Medicine and Biology Society, 2006, EMBS '06, 28$^{th}$ Annual International Conference of the IEEE, IEEE, Piscataway, NJ, USA, Aug. 30, 2006, pp. 6380-6383.
Stamatas, G.N., et al., "Noninvasive quantitative Documentation of Cutaneous Inflammation in Vivo Using Spectral Imaging", Proceedings of the Spie—the International Society for Optical Engineering Spie—In. Soc., Opt. Eng., USA, vol. 5078, No. 1, 2006, pp. 111-118.
Stamatas, G.N., et al. "In Vivo Measurement of Skin Erythema and Pigmentation: New Means of Implementation of Diffuse Reflectance Spectroscopy with A Commercial Instrument", The British Journal of Dermatology, Sep. 2008, LNKD-PUBMED: 18510669, vol. 159, No. 3, Sep. 2008 (2006-2009) pp. 683-690.
European Search Report, Application No. 10250571.6, dated Aug. 19, 2010.

* cited by examiner

*Primary Examiner* — Jacqueline Cheng (57) ABSTRACT

A method for measuring skin erythema and determining the efficacy of skin care treatment products utilizing digital images.

3 Claims, 7 Drawing Sheets

FIG. 8

METHOD FOR MEASURING SKIN ERYTHEMA

BACKGROUND OF THE INVENTION

1. Field of the Invention

The method of this invention relates to a method for measuring skin erythema. The method of this invention utilizes digital image analysis of conventional photos that can be acquired by inexpensive digital cameras. This method is useful for demonstrating the efficacy of skin care products intended for the prevention and/or reduction of erythema, even when such erythema is not apparent to the naked eye.

2. Description of the Prior Art

Skin inflammation is often manifested as skin redness (erythema). Erythema is frequently associated with diaper rash, acne, dermatitis, eczema and other skin conditions. Many skin care products are designed either to prevent inflammation, as in the case of sunscreens, or to reduce imflammation, as in the case of diaper rash ointments). Significant skin inflammation may be present even after use of such skin care products but may not be apparent to the naked eye. While in many cases, individuals suffering from such inflammation can report that the inflammation and irritation is still present after use of such products, infants or others who are not able to express themselves, can continue to endure symptoms despite treatment. There is, therefore, a need for a method that is capable of demonstrating the efficacy of such skin care products more accurately.

Skin erythema is primarily due to vasodilation and local increases in hemoglobin concentration. The hemoglobin concentration in skin can be evaluated using several methods.

Chromameters have been utilized for analyzing hemoglobin. Chromameters give values of standardized parameters for color evaluation: L*,a*,b*, with a* being used as an indicator of the "red" content and therefore related to skin erythema.

Spectrophotometers have been used in a method for analyzing hemoglobin based on diffuse reflectance spectroscopy, according to which the reflected light from skin is collected and analyzed into its spectral components. Spectral analysis algorithms have been used to calculate chromophore concentrations including oxy- and deoxy-hemoglobin (relating to erythema). Various light reflectance devices such as a Mexameter are also known for giving an erythema index.

Spectral imaging is a method that combines the spectral information with two-dimensional spatial information to calculate intensity maps corresponding to chromophore concentrations including oxy- and deoxy-hemoglobin. The analysis of digital color images of skin has also been utilized for analyzing hemoglobin.

All of the methods described above have deficiencies in their ability to measure inflammation to the degree required in order to ensure treatment of a skin condition causing inflammation. Reflectance-based methods only give point measurements and are limited by the size of the probe used in conjunction with the method. Spectral imaging is the most accurate method for mapping hemoglobin concentration but requires specialized and expensive equipment. Methods using digital image analysis do not take into appropriate consideration all optical parameters of the skin that contribute to the perception of erythema. Therefore, there is a continuing need for a method for measuring skin erythema.

SUMMARY OF THE INVENTION

The method of this invention provides a way in which to measure skin erythema including the following steps: a) acquiring a digital image of skin under orthogonal polarization conditions with a white calibration standard included in the field of view of the image; b) identifying median intensity values for a red, a green, and a blue channel for the white calibration standard; c) translating skin reflectance values given by the red, green, and blue intensity values of each pixel of the image to absorbance values by calculating the logarithm of the ratio of the white standard values, i.e., the pixel intensity of the white standard for each of the channels (red, green, blue) divided by the skin reflectance values, i.e., the pixel intensity values at the corresponding channels (red, green, blue) at each of the red green and blue channels separately, where the absorbance equals:

$$\log(I_{white}(red, green, blue)/I_{skin}(red, green, blue))$$

for all pixels representing skin; d) subtracting the red channel absorbance values from the green channel absorbance values: (Abs(green)−Abs(red)) for all pixels representing skin; e) subtracting the red channel absorbance values from the blue channel absorbance values: (Abs(blue)−Abs(red)) for all pixels representing skin; f) calculating the ratio of the value calculated at step (d) divided by the value calculated at step (e)ratio=(Abs(green)−Abs(red))/(Abs(blue)−Abs(red)), and g) building an intensity map of the ratio calculated at step (f).

The method of this invention also provides a way in which to demonstrate the efficacy of a skin care product including: acquiring a digital image of an area of skin and analyzing the skin according to the method described above; applying a skin care product to the same area of skin for an effective amount of time; and then at a later time, acquiring a subsequent digital image of the area of skin and analyzing the skin according to the method described above; and comparing the intensity maps of the images to demonstrate a reduction in erythema of the skin. The length of time between the first and second image acquisitions can vary depending upon the treatment or effect being evaluated. For example, the efficacy of a moisturizer or anti-inflammatory may be evidenced within a short period of time, on the order of minutes or hours. However, the efficacy of a long-acting active ingredient to ameliorate skin conditions such as an allergic reaction, contact dermatitis, acne or the like may be evidenced over a much longer period of time such as days, weeks or months.

The method of this invention also provides a means by which to demonstrate the mildness of a skin care product including: acquiring a digital image of an area of skin and analyzing the skin according to the method described above; applying a skin care product to the same area of skin for an effective amount of time; acquiring a subsequent digital image of the area of skin and analyzing the skin according to the method described above; and comparing the intensity maps of the images to demonstrate no increase in erythema of the skin.

DETAILED DESCRIPTION OF PREFERRED EMBODIMENTS

Various types of cameras may be used in the methods of this invention. Examples of such cameras include, but are not limited to, standard 35 mm cameras, cameras using instant developing film (such as those available from Polaroid Corporation, Cambridge, Mass. USA), and digital cameras. Preferably, a digital camera is used as it provides fast access to the images taken of the subject. It also allows the image to be displayed on a large monitor, enables the subject to easily enlarge areas of skin that are of particular interest (e.g., areas of the face), and allows the image to be printed in a report which can also include suggestions for products addressing any concerns the subject noticed upon examining the images. Examples of suitable digital cameras include, but are not limited to, those which take images of at least 1 million pixels, preferable at least 4 million pixels. Examples of such digital cameras include, but are not limited to, the Nikon D1X (Nikon, Tokyo, Japan) and the Fuji S1 (Fuji, Tokyo, Japan).

The following terms used herein have the meanings ascribed to them below:

"ORTHOGONAL POLARIZATION CONDITIONS": imaging conditions that include a first polarizer filter in front of the light source and a second polarizer filter in front of the camera lens with the two filters having their polarization axes orthogonal to each other.

"WHITE CALIBRATION STANDARD": a uniform white card corresponding to a certain % reflectance (e.g. 80%).

"MEDIAN INTENSITY VALUES": the arithmetic median of a group of pixel intensity values corresponding to a region of interest in the image.

"SKIN REFLECTANCE VALUES": pixel intensity values of an area of interest in the image corresponding to skin.

"ABSORBANCE VALUES": the light absorbance being defined by the equation: absorbance=log {(reflectance of the white standard)/(reflectance of the object of interest)}.

In one embodiment, the methods of this invention include the step of taking a polarized photograph of the subject. What is meant by "polarized photograph" is a photograph of the subject taken (i) with a light source that emits light through a polarizing filter and/or (ii) through a polarized filter that filters light prior to or after entering the camera's lens.

In one embodiment, the camera and one or more flash units, preferably two, are on about the same plane as the subject's skin to be photographed, and the flash units are placed so that the angle formed by each flash unit(s), subject's skin, and camera is about 35 to 55 degrees, such as about 45 degrees. In one embodiment, a polarizing filter is placed in front of each flash unit. What is meant by a "polarizing filter" is a filter that filters incoming light to emit substantially only polarized light. What is meant by the term "substantially," as used herein, is at least 75 percent, preferably 90 percent, and most preferably at least 95 percent. Examples of a polarizing filter include, but are not limited to, polarizing plates such as those available from Edmund Scientific (Barrington, N.J. USA), polarizing prisms such as Glan Thomson polarizing prisms, or a polarizing reflector that reflects light at about the Brewster angle. Polarizing filters may be linear or circular polarizing filters.

In another embodiment of the method of this invention, a light diffuser is placed between the flash unit and the polarizing filter.

In yet another embodiment of the method of this invention, a linear polarizing filter is used at the light source and the linear polarizing filter is arranged such that the electric field of the emitted light is about perpendicular (orthogonal) to the plane formed by the light source, the person's skin, and the camera.

In another embodiment of the method of this invention, the flash unit(s) are positioned on a vertical plane above the camera and the subject's skin so that the angle formed by the flash unit, subject's skin and camera is about 35 to 55 degrees, preferably about 45 degrees. The flash unit(s) are filtered with a linear polarizing filter that is placed with the transmitted electric field in the vertical direction (e.g., parallel to the plane). In this arrangement the surface glare from the skin is minimized, thus enhancing the subsurface features of the skin, such as erythema (redness), blood vessels, and pigmentation.

In one embodiment of the method of this invention, the photograph of the subject is taken both with a light source that emits lights through a polarizing filter and through a polarizing filter that filters the light prior to or after entering the camera's lens. When the polarizing filters are aligned perpendicular to each other (e.g., one horizontal and one vertical), subsurface features of the skin such as erythema, pigmentation, blood vessels, and hair, are visually enhanced and surface specular reflections (glare) are eliminated.

Image analysis requires: a) acquiring a digital image of skin under orthogonal polarization conditions with a white calibration standard included in the field of view of the image; b) identifying median intensity values for a red, a green, and a blue channel for the white standard; c) translating skin reflectance values given by the red, green, and blue intensity values of each pixel of the image to absorbance values by taking the logarithm of the ratio of the white standard values divided by the skin reflectance values at each of the red, green, and blue channels separately, where the absorbance equals the $$\log(I_{white}(red,green,blue)/I_{skin}(red,green,blue))$$

for all pixels representing skin; d) subtracting the red channel absorbance values from the green channel absorbance values for all pixels representing skin; e) subtracting the red channel absorbance values from the blue channel absorbance values for all pixels representing skin; f) taking the ratio of the value calculated at step (d) divided by the value calculated at step (e), and g) building an intensity map of the ratio calculated at step (f).

In one embodiment the constructed erythema intensity map may be presented as a grayscale intensity image. In another embodiment, colormaps, which are tables of correspondence between gray-scale intensity values on one side and projected colors on the other, can be used in which the each intensity value is represented by a color. Colormaps can be used to enhance features corresponding to particular ranges of erythema intensity (see example 5). In this way, a gray-scale image can be projected as a "pseudo-color"; the sequence of colors in a colormap can be selected so as to enhance the appearance of features corresponding to a particular gray-scale range.

The methods are useful for measuring erythema, which enables one to demonstrate the efficacy of anti-inflammatory skin care products, or to demonstrate the mildness of skin care products. As used herein, skin care products include, but are not limited to, creams, lotions, ointments, solutions and the like that are intended to be used as cleansers, moisturizers, sunscreens, anti-wrinkle compositions, anti-itch compositions, anti-inflammatory compositions, skin pigmentation products, or anti-acne products. For example, images may be taken prior to and after application of an anti-inflammatory cream. The images enable the consumer to see a reduction in the erythema associated with inflammation.

Likewise, if a product has not been effective in sufficiently reducing erythema, the methods of this invention will so demonstrate and assist in determining whether a treatment has been efficacious. The following examples serve to illustrate, but not to limit, the methods of this invention.

EXAMPLE 1

Efficacy of Anti-inflammatory Active Ingredients

Figure 1:
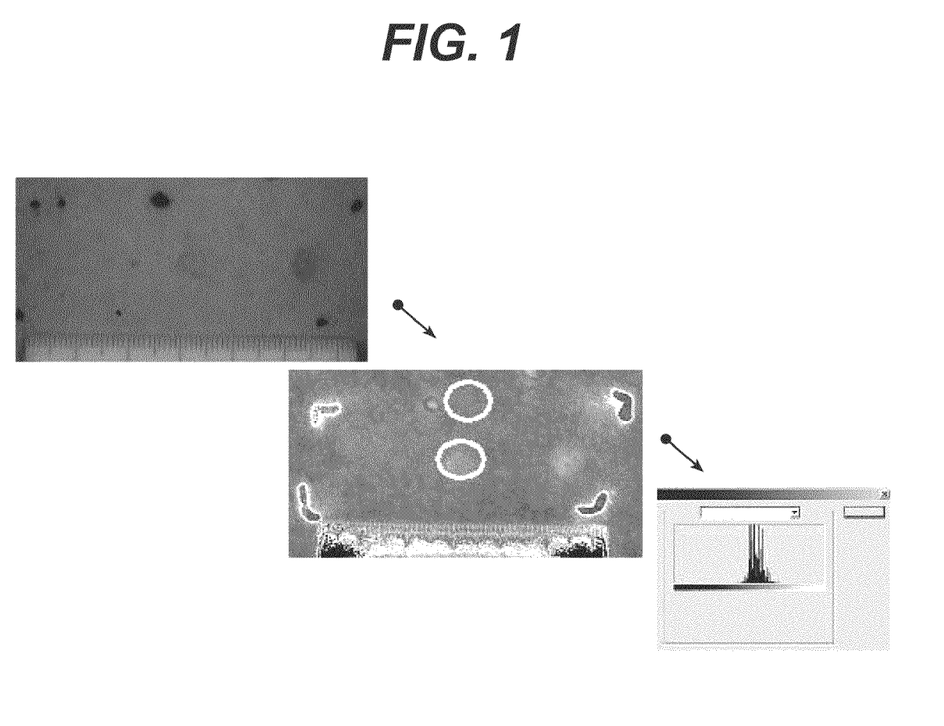
FIG. 1 shows the transformation of a skin image to an intensity histogram corresponding to each area on the image.
Figure 2:
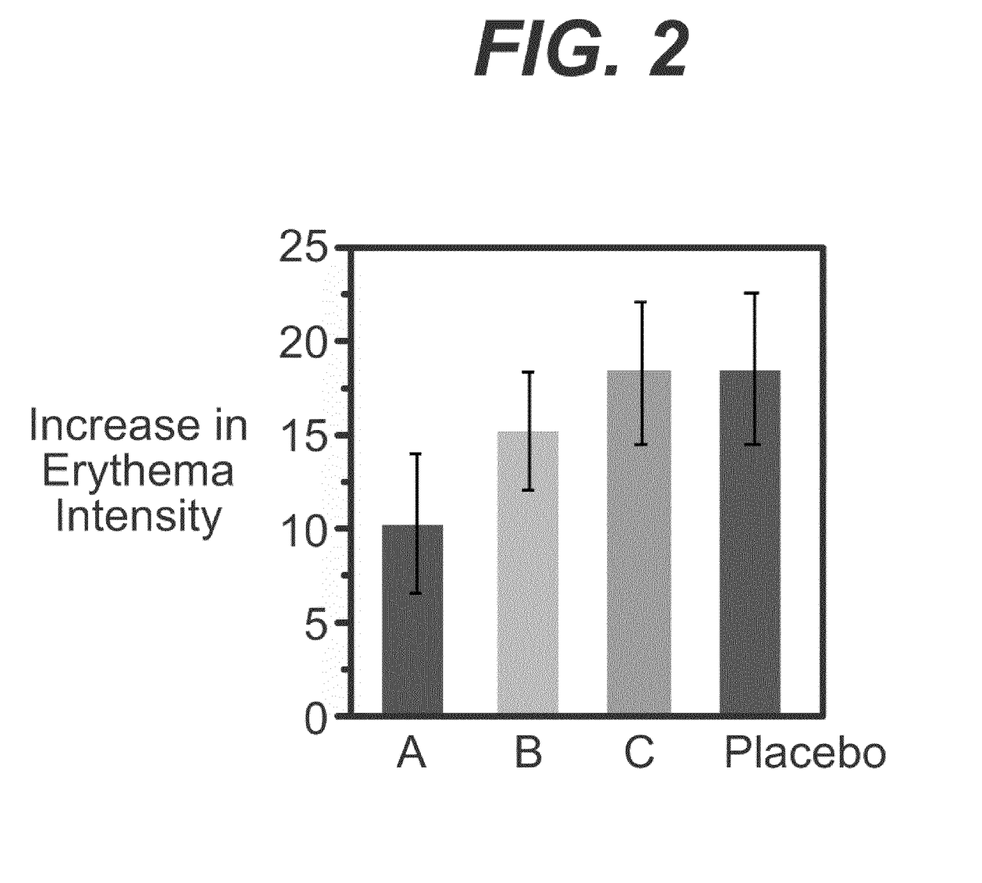
FIG. 2 is a graph demonstrating the average increase in erythema intensity on the skin of several subjects.

The anti-inflammatory activity of three natural extracts in a 70% ethanol/30% propylene glycol base (A=4% Jasmin extract/3% Sunflower extract, B=2% Jasmin extract/2% Sunflower extract, and C=1% Symatrix) was assessed versus the base alone. Four rectangular areas on the back of 6 volunteers were treated with either one of the tested formulations (A, B, C, placebo). Then three smaller round areas in each of the rectangles received UVB radiation at doses corresponding to 0.5, 1, and 1.5 MED. Images were acquired one day following the irradiation. The images were transformed using the method (and associated algorithm) of this invention to generate erythema intensity maps. Circular areas of interest were drawn around the marked skin sites and the mean, standard deviation, and median of the erythema intensity was calculated from the intensity histogram corresponding to each area (FIG. 1). The average increase in erythema intensity was calculated for all six subjects (FIG. 2). The results demonstrate that the method of this invention enables one to identify the most efficacious of the tested substances for anti-inflammatory activity and protection from sunburn.

EXAMPLE 2

Soothing Effect of Moisturizers

Figure 3:
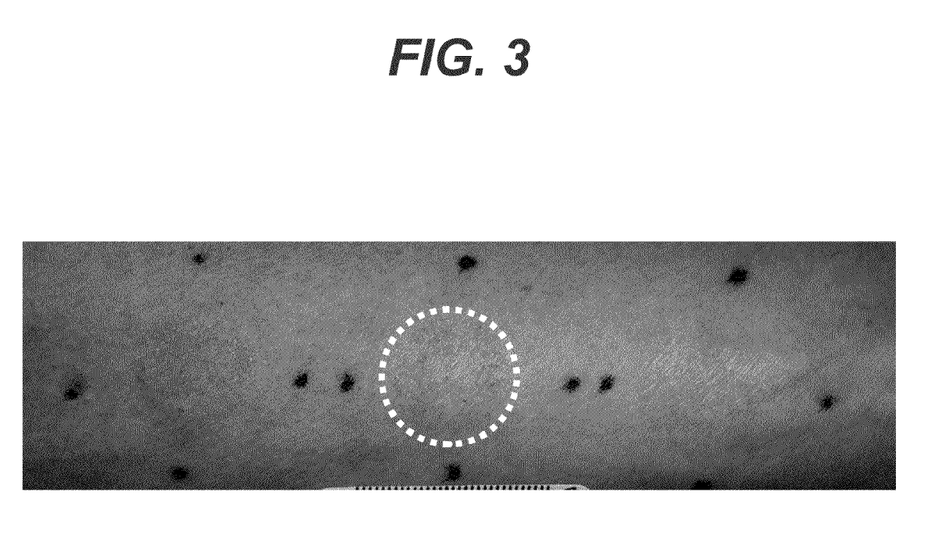
FIG. 3 is a photograph of the skin of a subject.
Figure 4:
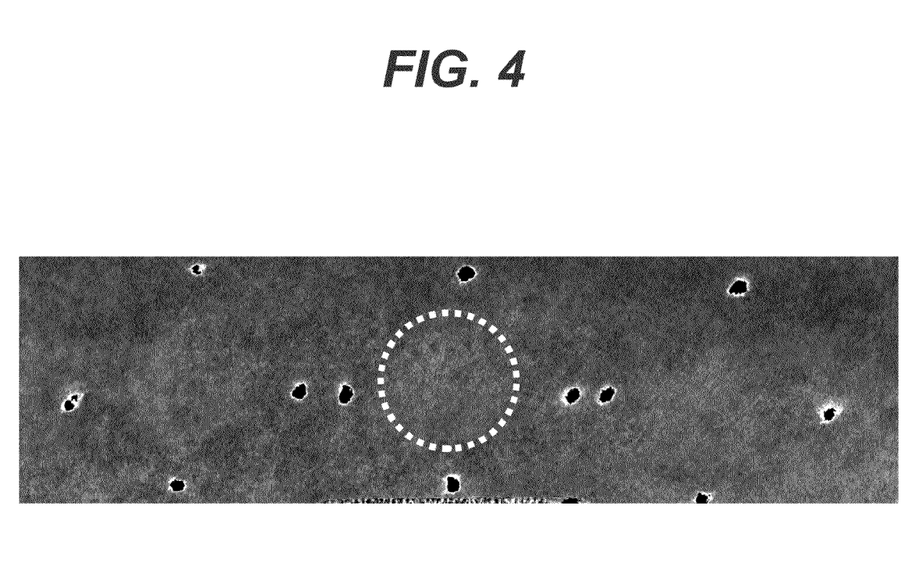
FIG. 4 is an erythema intensity map of the skin photographed in FIG. 3.

A study was performed to assess the effect of two moisturizers (A and B) on the treatment of skin irritation following the act of compromising the skin barrier. Three sites of the volar forearm of the volunteers were subjected to 10 tape stripes followed by treatment with 0.16 ml of 5% SLS (sodium lauryl sulfate) solution under occlusion for two hrs. Following patch removal, the tested substances were applied on the designated skin sites (2 $\mu l/cm^2$) and one site was kept untreated. The test substances were applied at the corresponding sites daily thereafter for four days. Images were taken daily during the duration of the study. The example in FIG. 3 shows the photo of the arm of a volunteer on day three. Erythema is evident on the sites. However, it is impossible to qualify the sites in terms of severity or evaluate the erythema quantitatively just by observing this image. The image was then analyzed by the method of this invention and the resulting erythema intensity map is shown in FIG. 4. The mean, standard deviation, and median of the erythema intensity can be calculated for each site. In this example, the sites from left to right exhibit erythema indices of 130 (moisturizer A), 132 (moisturizer B), and 134 (untreated) respectively with the neighboring skin having a value of 119. This example demonstrates that using the method of this invention, one can distinguish between moisturizers in terms of reducing erythema and can identify the most efficacious one.

EXAMPLE 3

Mildness Level of Cleansers

Figure 5:
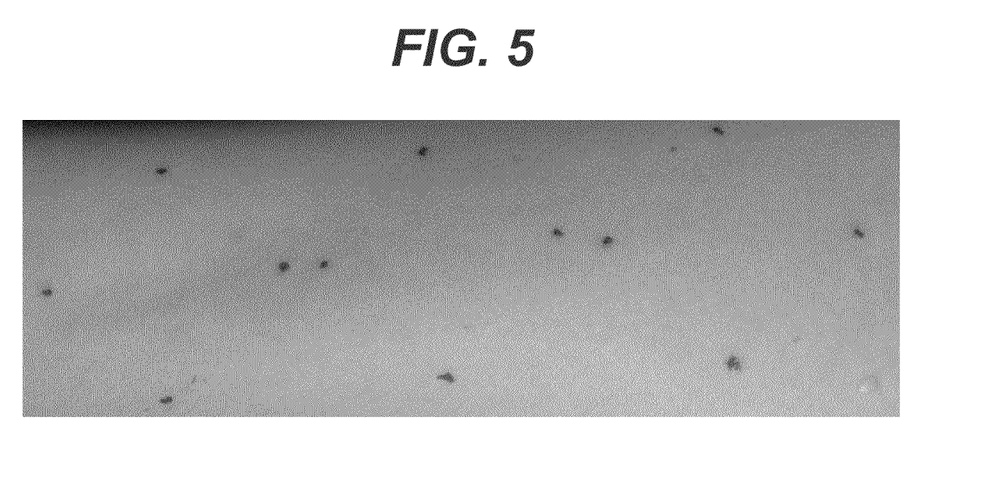
FIG. 5 is a photograph of the skin of a subject.
Figure 6:
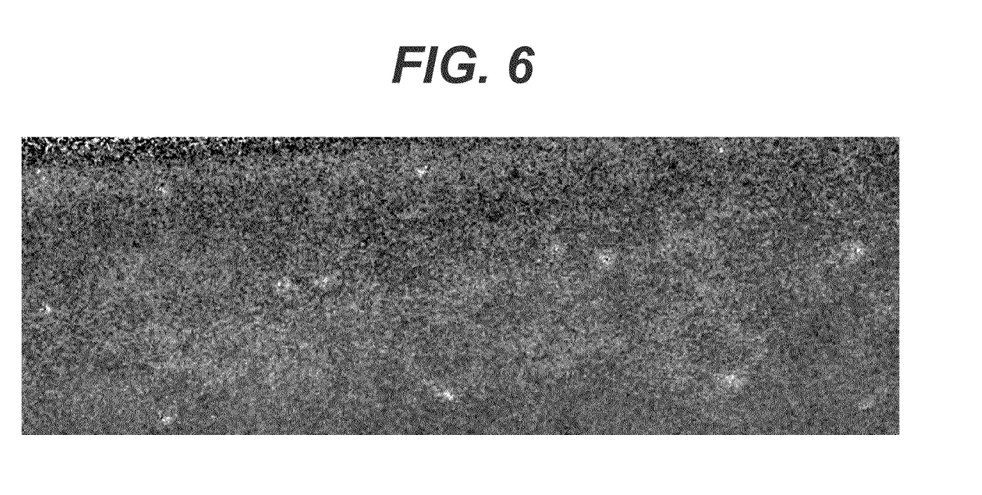
FIG. 6 is an erythema intensity map of the skin photographed in FIG. 5.

A study was performed to assess the mildness of a cleanser (Johnson's® Head-to-Toe Baby Wash, commercially available from Johnson & Johnson Consumer Companies, Inc., Skillman, N.J.) on the skin and compare it to water. Three sites of the volar forearm of the volunteers were treated with a) 25% dilution of the cleanser in distilled water, b) 10% dilution of the cleanser in distilled water and c) distilled water only, under occlusion for 3 hrs. Images were taken at baseline and at 1 and 2 days following treatment. The example in FIG. 5 shows the photo of the arm of a volunteer on day 2. It is difficult to distinguish any signs of erythema in all three sites of treatment. The image was then analyzed by the method of this invention and the resulting erythema intensity map is shown in FIG. 6. The mean, standard deviation, and median of the erythema intensity for each site were calculated. In this example the sites from left to right exhibit erythema indices of 182, 180, and 181 respectively with the neighboring skin having a value of 178. This example demonstrates that using the method of this invention, one can distinguish between cleansers or concentrations of cleansers in terms of their mildness on the skin.

EXAMPLE 4

Documentation of Subclinical Inflammation on the Face

Figure 7:
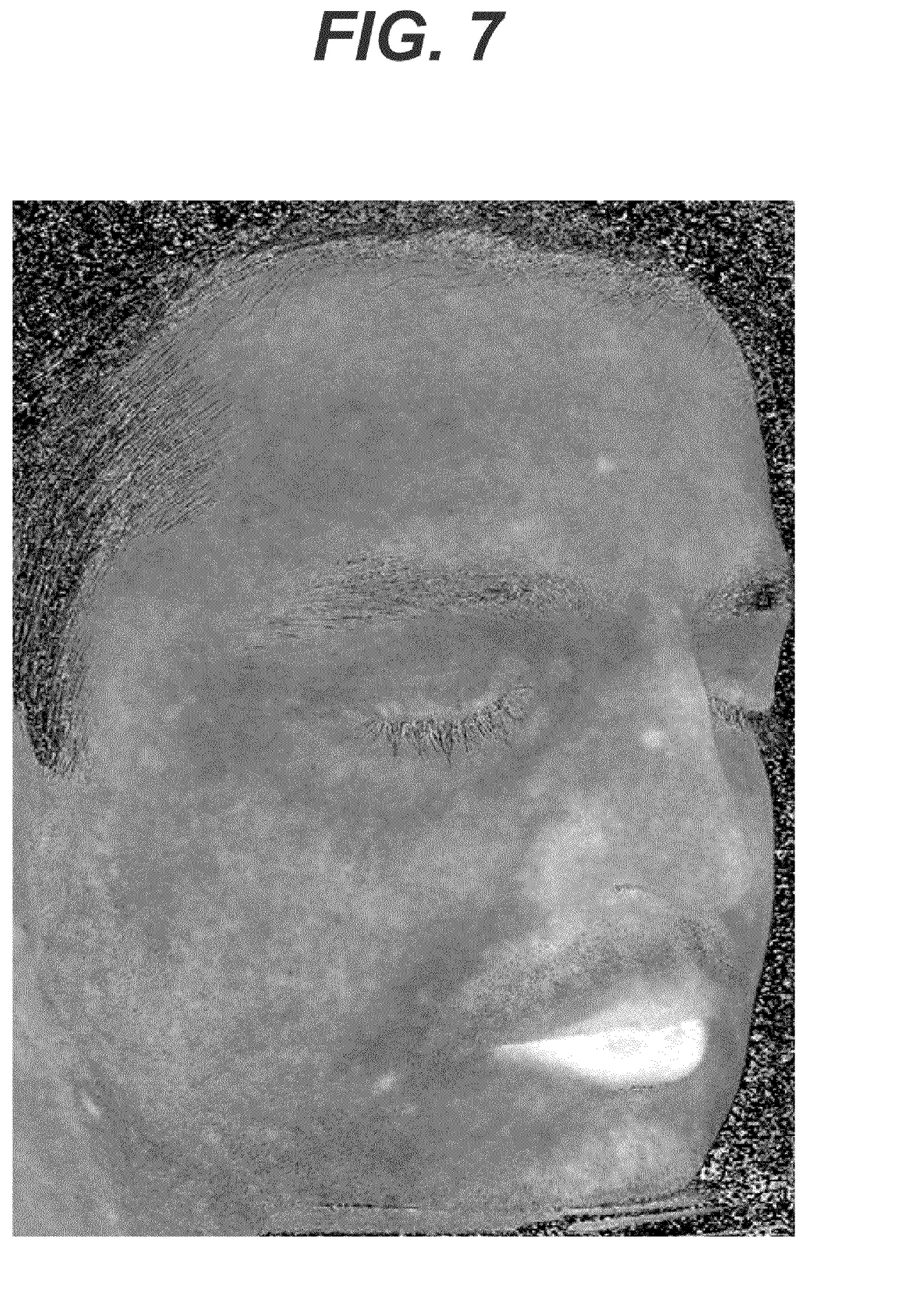
FIG. 7 is an erythema intensity map of the skin of a subject's face.

In the following example an orthogonal polarization image of a human face was analyzed by the method of this invention (with the associated algorithm). The erythema intensity map is shown in FIG. 7. Shadows and artifacts due to natural curvature of the face are canceled out on the erythema map. All inflammatory lesions that appear on the original image can be identified easily in the erythema map due to the increased contrast. The high intensity values on the lips area are indicative of the high blood concentration on the lips. Areas of sub-clinical inflammation are also evident in the erythema map, such as the diffuse erythema on the nose, the cheek, and the chin area. Moreover, areas of reduced concentration of oxyhemoglobin such as those around the eye and the nasolabial fold can be identified.

EXAMPLE 5

Use of a Custom Colormap

Figure 8:
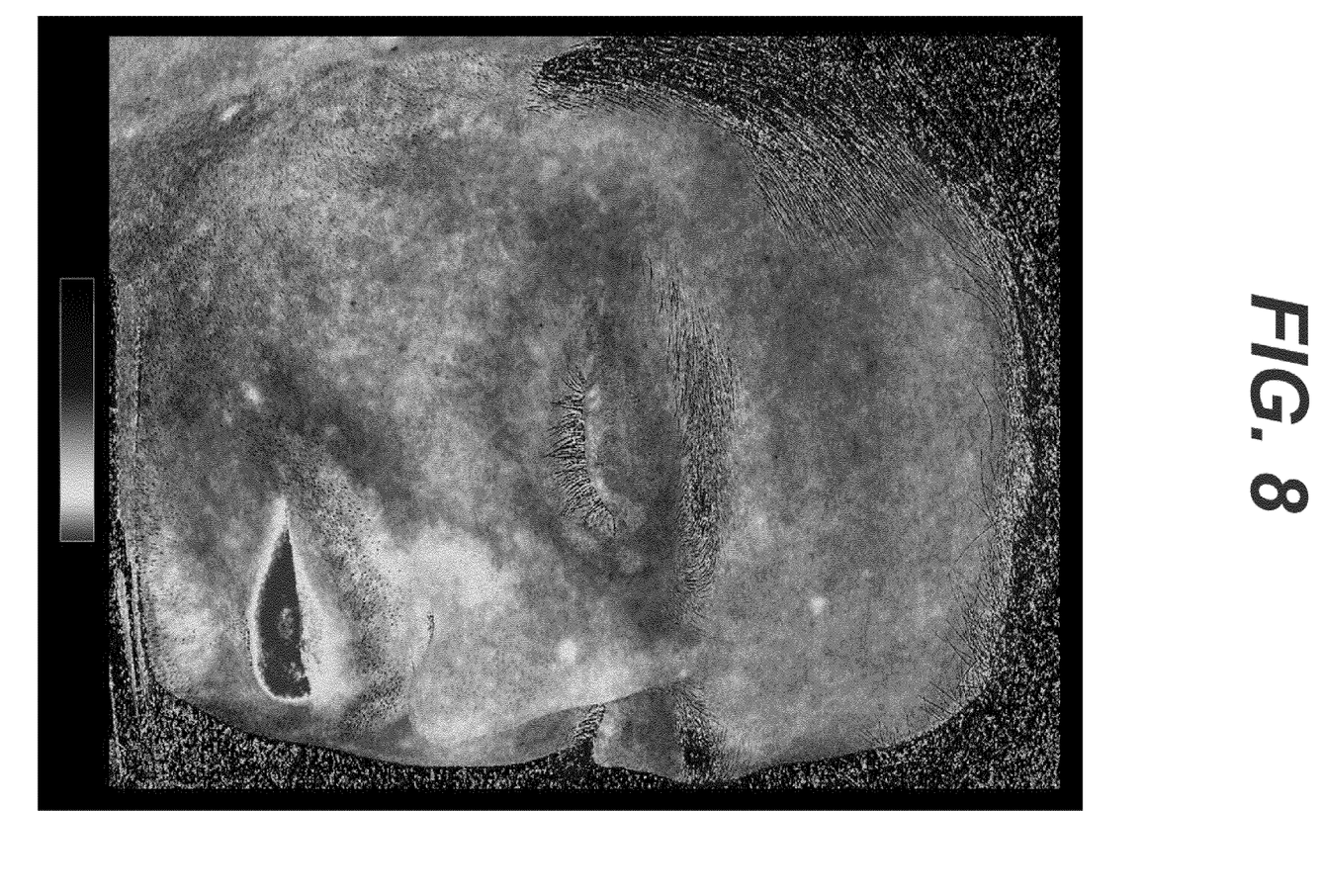
FIG. 8 is a color map of the erythema intensity map of FIG. 7.

For better visualization of the underlying subclinical erythema, the erythema intensity map can be displayed using a color-mapping scheme that can be customized depending on the application. An example is shown below (FIG. 8) of the erythema map of FIG. 7 using the color map indicated at the bottom of the image.

The Examples above demonstrate that using the methods of this invention, one can assess the mildness of cleansers, the activity of anti-inflammatories and other skin irritation treatments, and the efficacy of treatments against skin disorders such as but not limited to acne, rosacea, irritant contact dermatitis, allergic contact dermatitis, diaper dermatitis, atopic dermatitis, seborrheic dermatitis, etc. The methods can also be used for monitoring the progression of such disorders.

What is claimed is:

1. A method for measuring skin erythema comprising:
a) acquiring a digital image of skin under orthogonal polarization conditions with a white calibration standard included in the field of view of the image;
b) identifying median intensity values for a red, a green, and a blue channel for the white standard;
c) translating skin reflectance values given by the red, green, and blue intensity values of each pixel of the image to absorbance values by taking the logarithm of a ratio of the white standard values to the skin reflectance values at each of the red green and blue channels separately, where the absorbance equals:

$$\log(I_{white}(red,green,blue)/I_{skin}(red,green,blue))$$

for all pixels representing skin;
d) subtracting the red channel absorbance values from the green channel absorbance values for all pixels representing skin;
e) subtracting the red channel absorbance values from the blue channel absorbance values for all pixels representing skin;
f) calculating a ratio of the value calculated at step (d) to the value calculated at step (e); and
g) building an intensity map of the ratio calculated at step (f).

2. A method of demonstrating the efficacy of a skin care product comprising:
analyzing an area of the skin according to the method of claim 1;
applying a skin care product to the same area of skin for an effective amount of time;
making a subsequent analysis of the area of the skin according to the method of claim 1; and
comparing the intensity maps of the images to demonstrate a reduction in erythema of the skin.

3. A method of demonstrating the mildness of a skin care product comprising:
analyzing an area of the skin according to the method of claim 1;
applying a skin care product to the same area of skin for an effective amount of time;
making a subsequent analysis of the area of the skin according to the method of claim 1; and
comparing the intensity maps of the images to demonstrate no increase in erythema of the skin.

* * * * *

UNITED STATES PATENT AND TRADEMARK OFFICE
CERTIFICATE OF CORRECTION

PATENT NO. : 8,150,501 B2  
APPLICATION NO. : 12/411642  
DATED : April 3, 2012  
INVENTOR(S) : Georgios Stamatas It is certified that error appears in the above-identified patent and that said Letters Patent is hereby corrected as shown below:

In the Claims

Column 7

Claim 1, section (f),    line 23, delete "a" insert -- the --  
                                       line 23, after (d) insert -- divided by --  
                                       line 23, omit "to"

Signed and Sealed this  
Twenty-ninth Day of April, 2014

Michelle K. Lee  
*Deputy Director of the United States Patent and Trademark Office*